United States Patent
Audrain et al.

(10) Patent No.: US 11,901,067 B2
(45) Date of Patent: Feb. 13, 2024

(54) DISTRIBUTION SERVER FOR PATIENT DEVICES

(71) Applicant: Fresenius Vial SAS, Brézins (FR)

(72) Inventors: Jean-Baptiste Audrain, Voiron (FR); Loic Bith, Bourg de Peage (FR); Maciej Wroblewski, Lake Zurich, IL (US)

(73) Assignee: Fresenius Vial SAS, Brézins (FR)

( * ) Notice: Subject to any disclaimer, the term of this patent is extended or adjusted under 35 U.S.C. 154(b) by 493 days.

(21) Appl. No.: 17/054,136

(22) PCT Filed: Apr. 23, 2019

(86) PCT No.: PCT/EP2019/060270
§ 371 (c)(1),
(2) Date: Nov. 9, 2020

(87) PCT Pub. No.: WO2019/214929
PCT Pub. Date: Nov. 14, 2019

(65) Prior Publication Data
US 2021/0125713 A1   Apr. 29, 2021

(30) Foreign Application Priority Data
May 11, 2018   (EP) ..................... 18305579

(51) Int. Cl.
  *G06F 8/61* (2018.01)
  *G06F 11/36* (2006.01)
  (Continued)

(52) U.S. Cl.
  CPC ............ *G16H 40/40* (2018.01); *A61M 5/172* (2013.01); *G16H 20/17* (2018.01); *G16H 40/67* (2018.01);
  (Continued)

(58) Field of Classification Search
  CPC ........ G16H 40/40; G16H 20/17; G16H 40/67; G16H 70/40; A61M 5/172; A61M 2205/52; G06F 8/71
  See application file for complete search history.

(56) References Cited

U.S. PATENT DOCUMENTS 8,893,109 B2 * 11/2014 Birtwhistle ............... G06F 8/65
  717/170
10,213,547 B2 * 2/2019 Rosinko ................. G16H 40/67
(Continued)

FOREIGN PATENT DOCUMENTS

EP   3173957   5/2017
EP   3173966   5/2017

OTHER PUBLICATIONS

Anonymous, A component of Windows Server Windows Server Update Services Windows Server Update Services—Wikipedia (Feb. 6, 2018) (4 pages).
(Continued)

*Primary Examiner* — Thuy Dao
(74) *Attorney, Agent, or Firm* — Cook Alex Ltd.

(57) ABSTRACT

Distribution servers and methods are disclosed for downloading data sets to patient devices. The server has a network interface circuit, a memory and a processing circuit. The memory receives a data set, the data set having parameters to be used by software on the patient devices to perform patient-related functions. The data set has a software version indicator for the data set. A processing circuit compares the software version indicator of the data set to a current software version of the patient device and determines that an inequality exists. Based on this determination, the server distributes the data set to the patient device.

20 Claims, 7 Drawing Sheets

```
PUMP                  DATA SET
TYPE        =         TYPE      ←—300
DFV MAJOR   =         DFV MAJOR ←—302
DFV MINOR   ≥         DFV MINOR ←—304
CFV MAJOR   =         CFV MAJOR ←—306
CFV MINOR   ≥         CFV MINOR ←—308
```

(51) Int. Cl.
    *H04L 9/32*      (2006.01)
    *G06F 9/455*     (2018.01)
    *G16H 40/40*     (2018.01)
    *G16H 20/17*     (2018.01)
    *G16H 40/67*     (2018.01)
    *A61M 5/172*     (2006.01)
    *G16H 70/40*     (2018.01)
    *G06F 8/71*      (2018.01)

(52) U.S. Cl.
    CPC ........... *A61M 2205/52* (2013.01); *G06F 8/71* (2013.01); *G16H 70/40* (2018.01)

(56) References Cited

U.S. PATENT DOCUMENTS

| | | | |
|---|---|---|---|
| 2010/0037216 A1* | 2/2010 | Carcerano | G06F 8/65 717/173 |
| 2013/0036412 A1 | 2/2013 | Birtwhistle et al. | |
| 2015/0199485 A1* | 7/2015 | Borges | G16H 40/40 600/323 |
| 2015/0234649 A1* | 8/2015 | Sugiura | G06F 8/71 717/170 |
| 2016/0381142 A1 | 12/2016 | Borges et al. | |

OTHER PUBLICATIONS

International Search Report and Written Opinion, counterpart International Appl. No. PCT/EP2019/060270 (dated Jul. 30, 2019) (13 pages).

\* cited by examiner

```
              PUMP         DATA SET
              TYPE      =    TYPE       ← 300
           DFV MAJOR    =  DFV MAJOR    ← 302
           DFV MINOR    ≥  DFV MINOR    ← 304
           CFV MAJOR    =  CFV MAJOR    ← 306
           CFV MINOR    ≥  CFV MINOR    ← 308
```

FIG. 3

CASE 1:

```
         PUMP                              DATA SET
    ID  DFV  CFV  TYPE              ID  DFV  CFV  TYPE
    1   32   13    3   ←─────────── 1   32   13    3
    2   33   15    3   ←──────┘
```

FIG. 4

CASE 2:

```
         PUMP                   72         DATA SET
    ID  DFV  CFV  TYPE                ID  DFV  CFV  TYPE
    1   32   13    3   ←──────────── 1   32   13    3
             ↓                        2   42   23    3
    1   43   24    3   ←──────────┘
                                   74
```

FIG. 5

| PUMP SOFTWARE | | DFV DRUGLIB_FORMAT_VERSION |
|---|---|---|
| AGILIA VP MC | 1.3 | 026 |
| | 1.4 | 026 |
| | 2.2c | 027 |
| | 2.3 ROW | 027 |
| | 2.3 US | 030 |
| AGILIA VP STD | 2.2c | 016 |
| | 2.3 | 016 |
| AGILIA SP MC | 1.5 | 032 |
| | 1.6 | 032 |
| | 1.6a | 032 |
| | 2.2 | 033 |
| | 2.3 | 033 |
| AGILIA SP STD | 2.2 | 015 |
| | 2.3 | 015 |
| AGILIA SP TIVA | 2.2 | 033 |
| | 2.3 | 033 |
| AGILIA SP PCA | 3.1 | 035 |

FIG. 6

| PUMP SOFTWARE | | CFV CAREAREA_FORMAT_VERSION |
|---|---|---|
| AGILIA VP MC | 1.3 | 013☐ |
| | 1.4 | 013☐ |
| | 2.2c | 015☐ |
| | 2.3 ROW | 015☐ |
| | 2.3 US | 020☐ |
| AGILIA VP STD | 2.2c | 015☐ |
| | 2.3 | 015☐ |
| AGILIA SP MC | 1.5 | 013☐ |
| | 1.6 | 013☐ |
| | 1.6a | 013☐ |

| | PUMP SOFTWARE | CFV CAREAREA_FORMAT_VERSION |
|---|---|---|
| | 2.2 | 015☐ |
| | 2.3 | 015☐ |
| AGILIA SP STD | 2.2 | 015☐ |
| | 2.3 | 015☐ |
| AGILIA SP TIVA | 2.2 | 015☐ |
| | 2.3 | 015☐ |
| AGILIA SP PCA | 3.1 | 017☐ |

FIG. 7

DISTRIBUTION SERVER FOR PATIENT DEVICES

The present application is a U.S. National Stage of PCT International Patent Application No. PCT/EP2019/060270, filed Apr. 23, 2019, which claims priority to EP Application No. 18305579, filed May 11, 2018, both of which are hereby incorporated herein by reference.

BACKGROUND

Infusion pumps are used to administer drugs and other medicaments to patients, typically in a clinical setting. An infusion pump provides a controlled amount of the medicament over time to the patient. The amount is administered pursuant to parameters entered by a clinician into the pump using a pump user interface.

Drug libraries are used on infusion pumps to provide further configuration beyond the software released by the manufacturer of the device. Drug libraries can be user-configurable, for example by a pharmacist, and can include drug names, doses, limits to the upper and/lower ranges of administration parameters. When new software is released by a manufacturer and programmed into the infusion pumps, updated drug libraries are to be generated so that they are compatible with the new software. Frequent software releases, even of a minor nature, result in undesirable additional work for those programming the drug libraries.

BRIEF DESCRIPTION OF THE DRAWINGS

FIG. 3 is a table illustrating a set of criteria used to determine whether a data set is to be distributed to a patient device, according to an illustrative embodiment;

FIG. 4 is an illustration of a first case scenario for determining whether a data set is to be distributed to a patient device, according to an illustrative embodiment;

FIG. 5 is an illustration of a second case scenario for determining whether a data set is to be distributed to a patient device, according to an illustrative embodiment;

FIG. 6 is a table of software version indicators for a first function code, according to an illustrative embodiment;

FIG. 7 is a table of software version indicators for a second function code, according to an illustrative embodiment;

DETAILED DESCRIPTION OF ILLUSTRATIVE EMBODIMENTS

In some embodiments, a distribution system of data sets to patient devices is provided which is flexible with different configuration settings.

In some embodiments, a distribution server provides automatic re-distribution of a new data set which is due to a patient device in response to an upgrade/downgrade of the configuration of the new data set.

In some embodiments, a distribution system allows much broader distribution of appropriate data sets based on a patient device's specific parameters (such as type and software function codes) without updating a data set (collection of data set files) and pursuant to a distribution policy (the combination of the pump location and data set).

In some embodiments, pharmacist workload can be greatly reduced by allowing data sets to be deemed compatible with pumps when software on the pumps are updated with only a minor software revision.

In some embodiments, deploying a Dose Error Reduction System and pumps can be done independently due to the flexibility of allowing data sets having minor incompatibilities to nevertheless be used with software upgrades.

In some embodiments, a Virtual Machine Manager may be implemented for new software features without disturbing pumps implemented in the field and vice versa.

Figure 1:
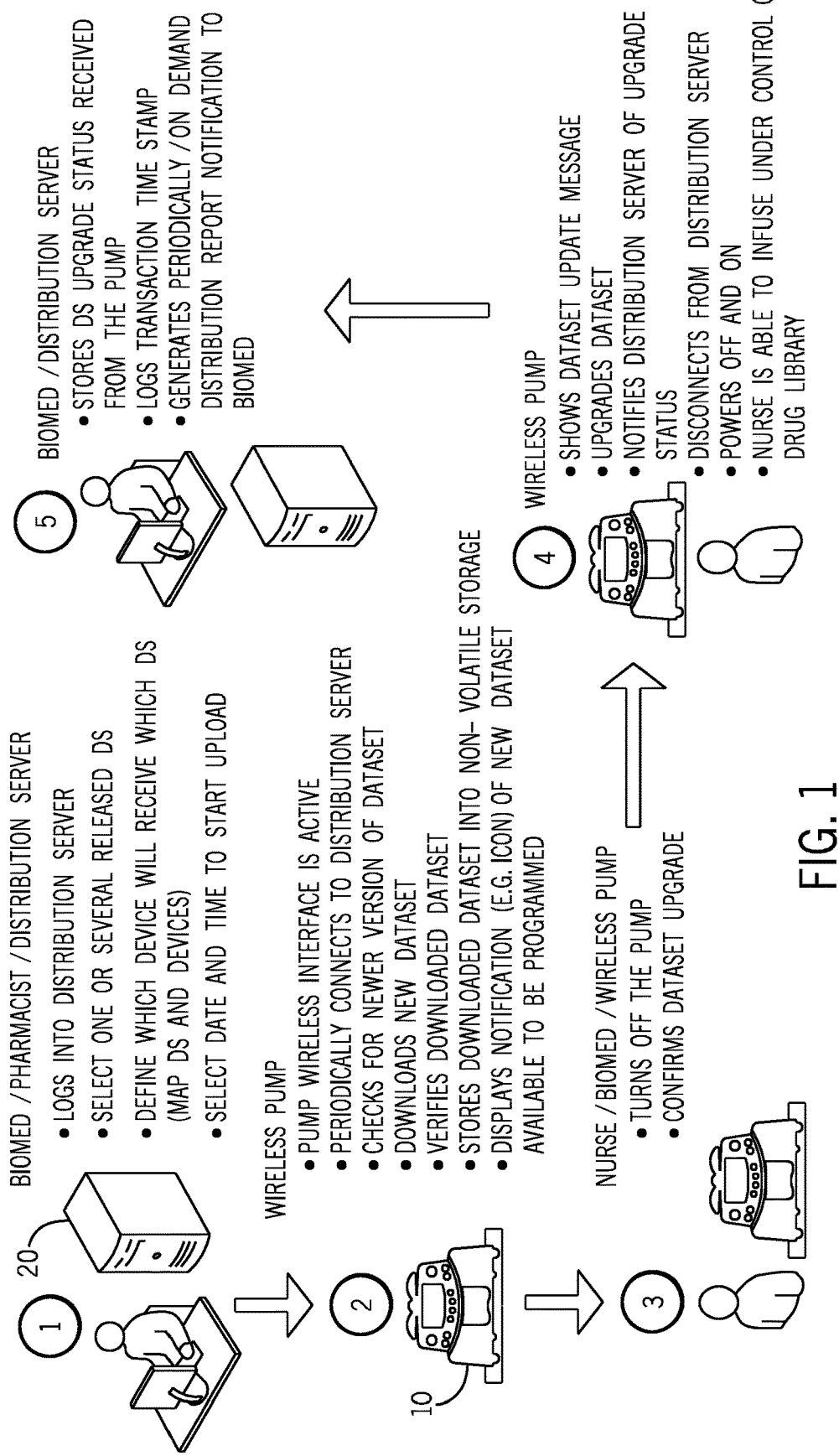
FIG. 1 is a flow diagram of a system and method for programming a dataset from a server computer to an infusion pump, according to an illustrative embodiment.

Referring now to FIG. 1, a flow diagram of a system for programming a patient device with a dataset from a server computer will be described. In this example, the patient device is an infusion pump 10, though in alternative embodiments the patient device may be any medical device, such as any device configured to provide medical functions or services to a patient (including a blood or organ donor) in any clinical, hospital, home care, or other setting, by way of invasive procedure (e.g., using a needle in a procedure) or otherwise. Infusion pump 10 may be any of a variety of infusion pumps, such as a large volume infusion pump, a patient-controlled analgesia (PCA) pump, elastomeric pump, syringe pump, enteral or parenteral feeding pump, insulin pump, etc. At Step 1 in FIG. 1, a user (e.g., a pharmacist, biomedical engineer, etc.) logs into a server computer 20 or terminal (e.g., pharmacy computer located or disposed in a pharmacy to be programmed by a pharmacist) in communication with server computer 20. The user selects one or more datasets to be programmed into or downloaded to infusion pump(s) 10. The dataset may comprise data that the infusion pump uses in its operation. For example, the dataset may be a library of drug programming parameters that provide default values and limits to a user's ability to program the infusion pump. For example, a data set may comprise hard limits and/or soft limits to different pump programming parameters, such as infusion rate, dose, infusion time or duration, etc. The limits of the data set may be different for different drugs, and may include a "drug X" data set for a drug not known by the data library. Once changes are made to the data set or library, server 20 may be used to remotely download, update, or otherwise program infusion pumps 10 (e.g., by care area, universally, etc.) with the new data set created by the pharmacist or other user. The user may select a date and time after which the infusion pump will receive the new dataset. The patient devices may be clinician-programmable infusion pumps, wherein the data set comprises hard and soft limits for parameters to be programmed by a clinician. At Step 2, in FIG. 1, infusion pump 10 may be configured for wired and/or wireless communication with a server computer 20. Each of pump 10 and server computer 20 may comprise a network interface circuit configured for network communications. Pump 10 is configured to transmit and server 20 is configured to receive a request for infusion pump data, such as a dataset, such as a drug library of infusion data. Infusion pump data requests may be initiated by infusion pump 10 and may occur periodically, intermittently, occasionally, every few minutes, several times per day, or at other regular or irregular frequencies. Pump 10 may be configured to request whether a newer version of a dataset is available for download from server computer 20 and to download the dataset. The downloaded dataset may be stored in non-volatile storage memory. Pump 10 may be configured to display a notification (e.g., an icon or other notification) that a new dataset is downloaded and available to be programmed.

At Step 3 of FIG. 1, a nurse, biomedical engineering staff, or other user may, upon seeing the notification, cycle the power on the pump to install or activate the new dataset. Pump 10 may be configured to confirm via a notification that a dataset is available for upgrading or updating. At Step 4, a user may command the pump to upgrade the dataset. Once the dataset is upgraded, pump 10 may notify server computer 20 of upgrade status (e.g., upgrade complete or successful, upgrade failed or error, etc.). Pump 10 may then disconnect from communications with server computer 20 for security purposes. After cycling the power, the nurse is able to infuse under control of the new dataset downloaded.

At Step 5, server computer 20 is configured to store the upgrade status received from pump 10, log the transaction time stamp (e.g., the time the pump was upgraded, the time the upgrade confirm message was received, or other time), and generate on demand or periodically a distribution report notification to another user, such as a biomedical engineering staff. Reports may be generated in a prescheduled manner or on-demand based on user inputs to the system. Reports may also be sent automatically, without requiring user input, on a scheduled basis, or in response to certain rules being met (e.g., alarm triggered, a certain number of alarms triggered, a certain number of override or reprogram events, etc.).

Figure 2:
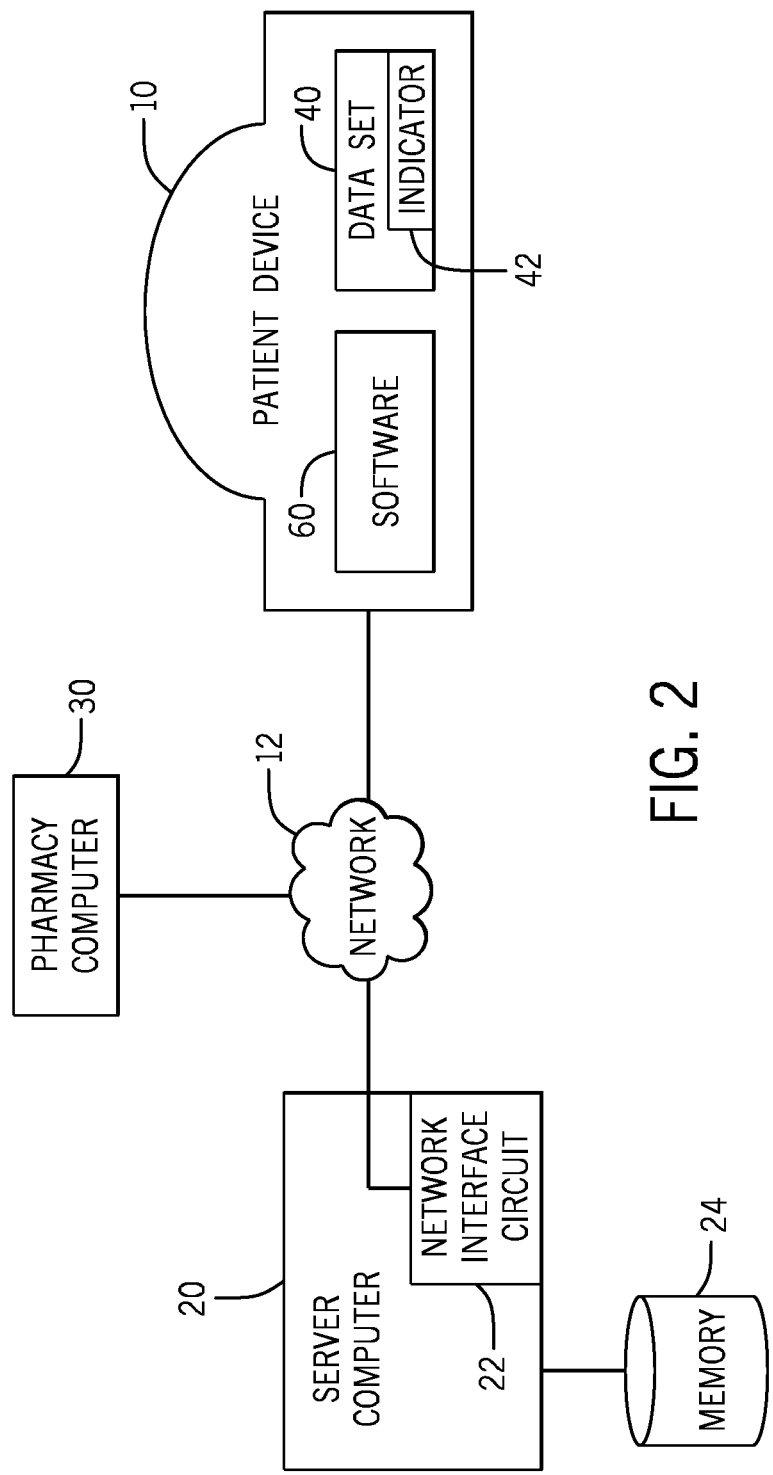
FIG. 2 is a block diagram of a distribution server, pharmacy computer, and patient device, for downloading data sets according to an illustrative embodiment.

Referring now to FIG. 2, a distribution server 20 for downloading data sets to patient devices will be described. Server 20 may comprise a network interface circuit 22 configured to communicate over a network 12 with one or more patient devices 10 and/or with a memory 24. Network interface circuit 22 may comprise one or more separate interface circuits configured for communication over simple or complex networks, such as a peer-to-peer network, a serial communication line, an Ethernet, the Internet, local area networks, personal area networks, a Wi-Fi network, a Bluetooth network, or other communication links. Memory 24 may be configured to receive over the network interface circuit from pharmacy computer 30 a data set. Pharmacy computer 30 may comprise a computer, server, terminal, or other computing device configured to receive user input from a pharmacist or other medical professional regarding the data in the data set. Various data sets may be generated using pharmacy computer 30 for different hospitals, clinics, floors, care areas, etc., according to a distribution policy.

Data set (shown distributed at data set 40) may comprise parameters, limits, configurations, values, or other data to be used by software 60 on the patient devices 10 to perform patient-related functions (e.g., treatment, blood component collection, etc.). In some embodiments, data set 40 is not operating software, but instead is used by operating software 60 to determine options a user may have for programming patient device 10. As mentioned, data set 40 may comprise a drug library having drug names and hard and/or soft limits for drugs to be infused, the limits being determined by a pharmacist. In some embodiments, data set 40 is configurable by an end user, such as a pharmacist, whereas software 60 is not user-configurable but instead is configurable only by a manufacturer or server of patient device 10. In some embodiments, changes to software 60 must be compiled to machine code and changes to data set 40 may be stored in a document format.

Data set 40 may comprise a software version indicator 42. Software version indicator 42 may comprise metadata or other data indicating a version of software 60 with which data set 40 was designed to operate. Software version indicator 42 may indicate compatibility between data set 40 and one or more particular versions of software 60. Software version indicator 42 may comprise one or more codes, hex values, or other data, as will be described in exemplary embodiments with reference to FIGS. 3-7.

In some embodiments, server computer 20 comprises a processing circuit configured to receive a data set from pharmacy computer 30 having a software version indicator 42 and to store the data set in memory 24. Server computer 20 is further configured to receive a current software version (which may also be an indicator, code, metadata, or other form of data) for software 60 on patient device 10. Server computer 20 may be configured to compare the software version indicator of the data set to the current software version of the patient device and to determine that an inequality exists between the software version indicator for the data set and the current software version of the patient device. For example, server computer 20 may determine that the current software version of the pump is numerically greater-than-or-equal-to the software version indicator of the data set. If so, server computer 20 may be configured to distribute the data set to the patient device based on the determination of the inequality. Other inequalities may be used, such as less-than-or-equal-to, not equal to, greater than, less than, etc. In some embodiments, newer software versions will have higher software version numbers.

In some embodiments, server computer 20 determines that if the software version indicator of the data set is less than or equal to the current software version of software active or operating on patient device 10, the data set is operable with said software and therefore the data set can be distributed (e.g., downloaded and/or programmed, activated, etc.) to the patient device. In contrast, if the software version indicator of the data set is greater than the current software version of the software on patient device 10, server computer 20 determines that the data set is not operable with said software and therefore the data set is not distributed.

The description may be better understood with reference to FIG. 3. FIG. 3 is a table illustrating a set of criteria that are used to determine whether a data set is to be distributed to a patient device. Server computer 20 may be configured or programmed to apply one or more of the criteria (e.g., equality, inequalities, or other criteria) to data. Each time a software version is created, it is given a version number or code by the person generating the program. The code may comprise five components in this embodiment: Type, DFV Major, DFV Minor, CFV Major and CFV Minor. Type refers to the type of pump that the software is designed for, such as a syringe pump, a bag-type infusion pump, a Patient Controlled Analgesia pump, a particular model of these pumps, etc. Major refers to a major or significant software revision, such as one that effects pump compatibility with a certain set of pump configuration data and/or data sets. If the programmer updates the software and changes (e.g., increments) the major code, it is an indication that an old data set cannot be applied on that pump (i.e., the parameters listed in the data set are not applicable and the pump will not work with them). A major change may be one that introduces a new feature to the pump. Minor refers to a less significant software revision (e.g., a bug fix, a less important parameter such as screen brightness, etc.). If the programmer updates the software and changes the minor code but not the major code, it is an indication that the old data set is still compatible with the pump. Minor and major codes may progress numerically, for example M=1, m=1; M=1, m=2; M=1, m=3; M=2, m=1; M=2, m=2 . . . .

In some embodiments, a change in the major software version code indicates an update in pump controls or pump mechanics that may cause introduction of a new or major data structure update or redesign. In some embodiments, a change in the minor software version code indicates an update in pump functionality and/or pump parameters not related to the data set, and/or a change in which the data set-related data structure is preserved.

DFV refers to Drug Library Format Version and CFV refers to Care Area Format Version. These codes are programmable by a human programmer to indicate the version of different portions of the software code which operate different functions on the patient device. In this manner, the DFV and CFV are parameters which are pre-defined for each software version. DFV and CFV may be embedded in the software configured on the pump. DFV and CFV may be determined automatically, in accordance to the predefined values, based on pump type and software. In one example, a first portion of the software (identified as the DFV portion) may be updated to a new version while a second portion of the software (identified as the CFV portion) may be left unchanged. In this case, the DFV codes (Major and/or minor) would be incremented or otherwise changed while the CFV codes (Major and minor) would remain unchanged The software version indicator of the data set and the current software version of the patient device may each comprise a first function code associated with software operating a first set of functions on the patient device (e.g., functions relating to storing, updating and user interface with a data set or drug library) and a second function code associated with software operating a second set of functions on the patient device (e.g., functions relating to selecting and configuring the patient device for operation based on which care area is chosen for the device, such as intensive care, primary care, surgery, etc.).

A first criterion 300 compares a pump type of a pump to a pump type identifier of the data set. If the pump type and pump type identifier are equal, equivalent, numerically or otherwise, the criterion is met. In this embodiment, a data set is distributed in the case where all criteria in the table are met, though in alternative embodiments, one or more of these or other criteria are used linked by AND, OR or other logic to determine when a data set is to be distributed.

Criterion 302 compares DFV Major of the pump to DFV Major of the newly created or updated data set. If the two are equivalent, the criterion is met. Criterion 304 compares DFV minor of the pump to DFV minor of the newly created or updated data set. If DFV minor of the pump is greater than or equal to DFV minor of the data set, the criterion is met. Criterion 306 compares CFV Major of the pump to CFV Major of the newly created or updated data set. If the two are equivalent, the criterion is met. Criterion 308 compares CFV minor of the pump to CFV minor of the newly created or updated data set. If CFV minor of the pump is greater than or equal to CFV minor of the data set, the criterion is met. In this example, when all criteria are met, server 20 determines that the data set is to be distributed to the pump. In some embodiments, the data set is distributed to the patient device based on a determination that the inequality exists for both the first function codes (e.g., DFV Major) and the second function codes (e.g., CFV Major). Each of DFV Major, DFV Minor, CFV Major and CFV Minor may be portions of a software version indicator or current software version, and each may be considered codes within the software version code.

Referring now to FIG. 4, a first case of determining whether a data set is to be distributed to a patient device will be described. In this example, to select an appropriate data set pursuant to a distribution policy, server computer 20 compares the following parameters: pump type, major version of the first function code (e.g., DFV Major) and major version of the second function code (e.g., CFV major). If those parameters are equal on both sides (pump and data set), server computer 20 will check their respective minor versions of the first and second function codes. Server computer 20 will set the new target data set for the pump if first minor function codes and/or second minor function codes are equal or if the pump minor codes are greater than the data set minor codes (maximum value).

Referring again to FIG. 4, this example shows a data set with a software version indicator having five components: DFV=3 2, CFV=1 3 and Type=3 as the new target data set for two same pump types with different software versions, with pump 1 having a software version of DFV=3 2, CFV=1 3 and Type=3 and pump 2 having a software version of DFV=3 3, CFV=1 5 and Type=3. In this scenario, Type, Major and Minor DFV and CFV values match corresponding data set values and therefore server computer 20 determines that the data set is to be distributed to pump 1. Pump 2 has Type and Major DFV and CFV values equal to or matching those of the data set but pump Minor DFV (=3) is greater than data set minor DFV (=2). Also, pump 2 Minor CFV (=5) is greater than the data set Minor CFV (=3). Since both pumps meet the distribution criteria set forth in FIG. 3, server computer 20 indicates that this data set is to be distributed to both pumps 1 and 2.

Referring now to FIG. 5, a second case of determining whether a data set is to be distributed to a patient device will be described. As in the first example, to select an appropriate data set pursuant to a distribution policy, server computer 20 again uses the criteria of FIG. 3. This second case shows that memory 24 has a plurality of data sets, data set ID 1 and data set ID 2. Data set ID 1 has a Major DFV code of 3, a Minor DFV code of 2, a Major CFV code of 1, a Minor CFV code of 3 and a Type of 3. Data set ID 2 has a Major DFV code of 4, a Minor DFV code of 2, a Major CFV code of 2, a Minor CFV code of 3 and a Type of 3. Pump ID 1 has a Major DFV code of 3, a Minor DFV code of 2, a Major CFV code of 1, a Minor CFV code of 3 and a Type of 3. As indicated by line 72, pump ID 1 will receive the data set because all codes match/are equal. Pump ID 1 will not receive data set ID 2 because Major DFV and CFV codes of 4 and 2, respectively, do not match those of pump ID 1 (which are 3 and 1, respectively).

FIG. 5 illustrates another aspect of the present disclosure at line 74. In some embodiments, the system allows automatic redistribution of a new data set, such as data set ID 2, due to pump configuration upgrade/downgrade or other change, for example, by way of a software update. Server computer 20 may be configured to receive an indication that the patient device ID 1 has an updated software version. Server 20 may be configured to compare the updated software version to a plurality of data sets in the memory, each data set having a different software version indicator, such as data set ID 1 having software version indicator comprising 32 13 3 and data set ID 2 having a software version indicator comprising 42 23 3. Server computer 20 may be configured to determine at least one data set having a software version indicator (which may be a portion of the string of digits shown) which is numerically less than or equal to the updated software version. In this case, data set DFV Minor is 2, which is less than or equal to updated pump DFV 3 and data set CFV Minor is 3, which is less than or equal to updated pump CFV Minor of 4. Therefore, server computer 20 determines that data set ID 2 is now ready to be distributed to upgraded pump ID 1. Automation can be applied to one or more of the steps of receiving the indication of an updated software version, comparing the updated software version to a plurality of data sets, applying criteria such as those in FIG. 3, determining that a data set is to be distributed, and distributing the data set. These one or more steps can be automated by being performed automatically by the patient device and/or server computer 20 without requiring manual user input (for example, by way of a user interface to either computer or to computers in communication therewith).

Referring now to FIGS. 6 and 7, exemplary DFV codes (FIG. 6) and CFV codes (FIG. 7) are shown. Table 600 shows patient device types 602, such as different types of infusion pumps (e.g., syringe pumps or SPs, volume-type bag pumps or VPs, Total Intravenous Anesthesia (TIVA) pumps, Patient Controlled Analgesia (PCA) pumps, etc.). Each pump type may be associated with different software versions 604, such as version 1.3, 1.4, 2.2c., 2.3 ROW, etc. Software versions 604 may serve as software version indicators in some embodiments described herein and may be used in the criteria such as those shown in FIG. 3. In other embodiments, software version indicators may take the form of format version codes 606. Codes 606 comprise, in this embodiment, four characters such as 0, 2, 6 and □, with the last character representing an empty character when returned by a command, before the \r\n. Any one or more of the characters, codes, or indicators shown in FIGS. 6 and/or 7 may be used in the criteria described herein. The format version codes in FIGS. 6 and 7 comprise a first two digits 608 which refer to or indicate a major software release and a second two digits 610 which refer to or indicate a minor software release.

In some embodiments, two data sets that share the same to first digits shall be compatible. A data set uploader computer will distribute to a pump a data set in the case where the two digits used for the major release match, even if the 2 digits used for the minor release do not. In some embodiments, compatibility means that a pump can only receive a data set with a lower minor version and/or equal minor version, but not a higher one.

In some embodiments, server computer 20 may be programmed with the following algorithm as a system, method or means to apply criteria of software versions to determine whether a data set is to be distributed to a pump.

IF dataset_pump_type==pump_type
AND dataset_cfv_major==pump_cfv_major
AND (dataset_cfv_minor==pump_cfv_minor OR dataset_cfv_minor
closest inferior value from pump_cfv_minor)
AND dataset_dfv_major==pump_dfv_major
AND (dataset_dfv_minor==pump_dfv_minor OR dataset_dfv_minor
closest inferior value from pump_dfv_minor),
THEN, dataset is to be distributed to pump.

In one example, when a Dose Error Reduction System (DERS) product, such as a pharmacy computer, server computer 20, or other computer, wishes to create a data set (e.g., drug library, etc.) that is compatible with a certain pump, the data set may comprise in the data set file a DFV/CFV code pair chosen from the tables of FIGS. 6 and 7 that correspond to the targeted pump. In this manner, all codes within the software version indicator will be equal. When a data set uploader product or uploader component, as part of a product, is to distribute a data set file that fits to a patient device, the uploader product reads the DFV/CFV pair in the data file itself and sends the data set file to the targeted pump or pumps, according to the DFV/CFV pair that has been read. A DFV/CFV pair may also be used by server computer 20 to add a pump to a memory of the server computer (e.g., to register the pump with server computer 20). Server computer 20 reads the DFV/CFV pair and reads a pump ID and/or generates a pump ID for storage in the memory. In another example, when a new software is released for a particular pump type, a new DFV/CFV pair is written or chosen by a programmer and added to the tables of FIGS. 6 and 7, which may be stored in memory 24 and/or other computers in communication with network 12 (FIG. 2).

Figure 9:
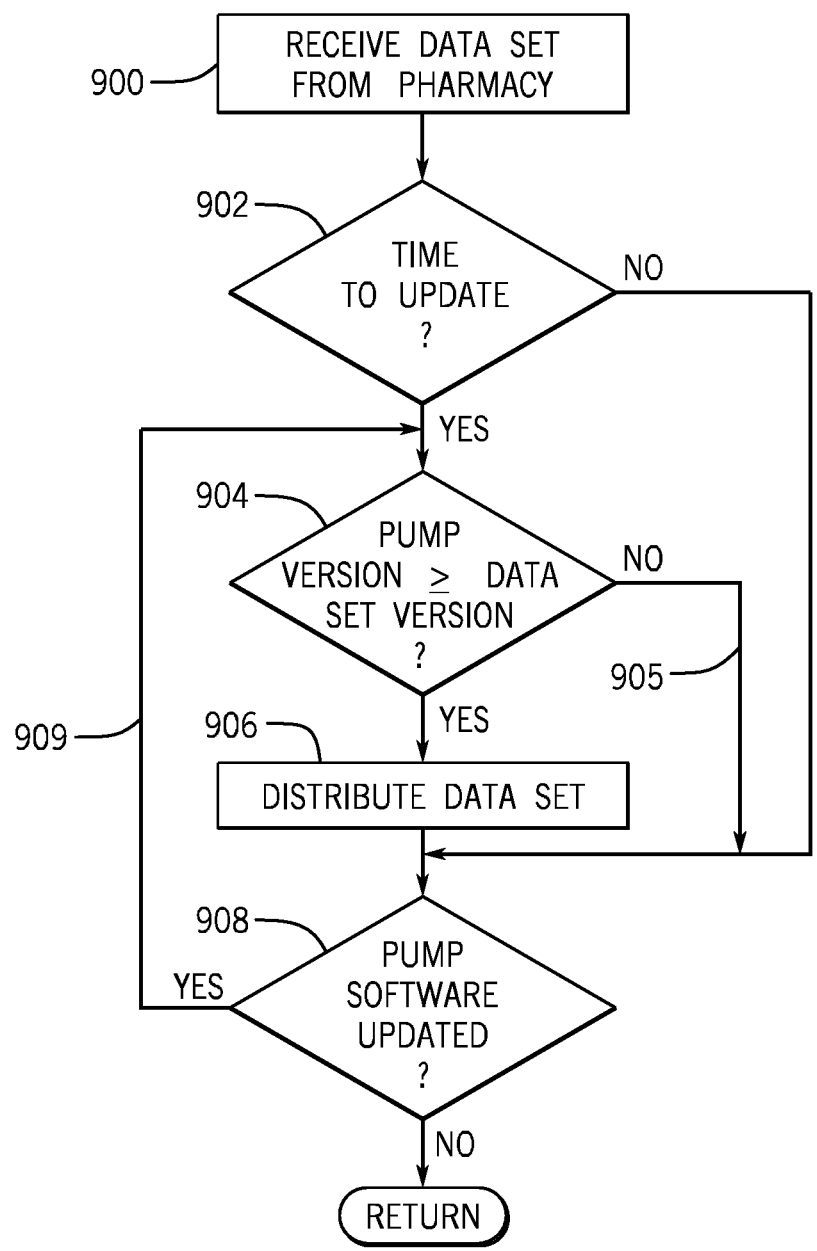
FIG. 9 is a flowchart of a method for determining if a data set is to be distributed to a pump, according to an illustrative embodiment.

Referring now to FIG. 9, a method of determining if a data set is to be distributed to a patient device will be described. At a block 900, a memory of a distribution server is configured to receive over a network interface circuit a data set, the data set comprising parameters to be used by software on the patient devices to perform patient-related functions. The data set may comprise a software version indicator as part of the data set file. The memory may also be configured to receive a current software version for a patient device. At a block 902, server computer and/or patient device may be configured to determine if it is time for a data set update. In certain examples, an initial installation of a data set occurs when a location (e.g., a hospital, clinic, doctor's office, etc.) has not previously used a patient device and/or associated drug library/data set. After installation, updates can occur periodically and/or aperiodically (e.g., update once a week, once a month, on trigger and/or demand, etc.). Updates may occur more frequently at a location that has never used a particular data set before and less frequently if the location has used a previous version of the data set with the same or different vendor and understands their settings, preferences, etc., for the data set, for example.

If server computer and/or patient device determine it is time to update a data set on a patient device, server computer is configured (block 904) to compare the software version indicator of the data set to the current software version of the patient device. As described herein the comparison may be to one or more components of the software version indicator, such as major and/or minor software change indicators, codes for one or more different portions of the software controlling different functions, codes in plain language "revision 1.1, 1.2, etc.", numerical codes (13, 23, etc.), or other codes or data. Further, any number of different criteria may be applied at step 904, such as equalities, inequalities, numerical or non-numerical relationships, or other criteria.

At branch 905, server computer determines the data set is not to be distributed to the patient device based on the comparison in block 904. In this case, processing proceeds to block 908 (with optional additional processing in the interim). At block 908, server computer determines whether pump software has been updated such that criteria in block 904 might now be met. Server computer may be configured to receive an indication that the patient device has an updated software version, which may be communicated by the patient device to the server in an ad hoc communication, in response to a query from server computer, or in another manner. Without receiving manual user input, server computer 20 automatically compares the software version indicator of the data set to the updated software version by returning to block 904. In this case, it is determined (as with Case 2 described in FIG. 5, line 74 described above) that the data set is to be distributed to the patient device based on the comparison to the updated software version. At block 906, server computer distributes the data set to the patient device based on the determination that the data set is to be distributed to the patient device.

As shown in block 904, after branch 909, the processing circuit of server computer 20 determines the data set is to be distributed to the patient device in the case where an inequality exists between the software version indicator of the data set and the updated software version.

In some embodiments, the memory is configured to store a plurality of data sets, each having respective software version indicators and the processing circuit is configured to identify at least two data sets compatible with the patient device. In this case, the processing circuit is configured to distribute one of the two data sets having a greater software version indicator (or more recent software release date) than the other of the two data sets.

In various embodiments, the data set further comprises a device type indicating a type of patient device, wherein the software version indicator of the data set and updated software version of the patient device each comprise a first software version code and a second software version code. The data set is distributed to the patient device based on a determination that the first software version codes are equivalent and the second software version codes have an inequality.

Figure 8:
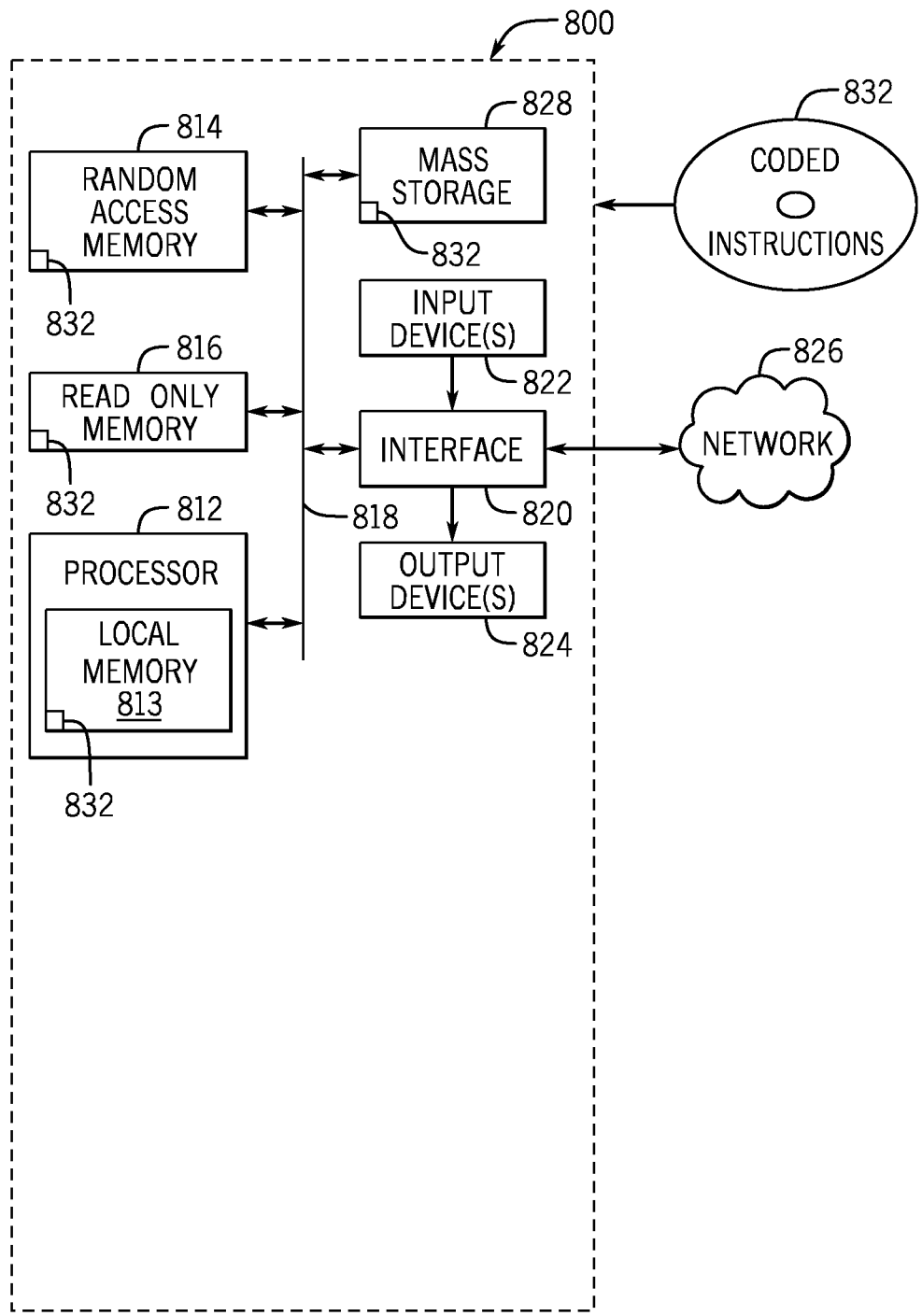
FIG. 8 is a block diagram of a processing circuit, one or more components of which may be used in the computers or other processing components described herein.

FIG. 8 is a block diagram of processing circuit components, one or more of which may be used in the computing devices described herein (e.g., server computer, pharmacy computer, patient device, uploader computer, etc.). In alternate embodiments, the systems and methods described herein may be implemented on a single server computer, a plurality of server computers, a server farm, a cloud server environment, or using other computer resources. Server 20 and patient device 10 may comprise analog and/or digital circuit components forming processing circuits configured to perform the steps described herein. The processing circuits may comprise discrete circuit elements and/or programmed integrated circuits, such as one or more microprocessors, microcontrollers, analog-to-digital converters, application-specific integrated circuits (ASICs), programmable logic, printed circuit boards, and/or other circuit components. Server 20 and patient device 10 may each comprise a network interface circuit configured to provide communications over one or more networks with each other and/or with other devices. The network interface circuit may comprise digital and/or analog circuit components configured to perform network communications functions. The networks may comprise one or more of a wide variety of networks, such as wired or wireless networks, wide-area, local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

FIG. 8 is a block diagram of an example processor platform 800 capable of executing the instructions described herein and/or to implement the example systems described herein. The processor platform 800 can be, for example, a server, a personal computer, a mobile device (e.g., a cell phone, a smart phone, a tablet such as an iPad™), a personal digital assistant (PDA), an Internet appliance, or any other type of computing device.

The processor platform 800 of the illustrated example includes a processor 812. The processor 812 of the illustrated example is hardware. For example, the processor 812 can be implemented by one or more integrated circuits, logic circuits, microprocessors or controllers from any desired family or manufacturer. In the illustrated example, the processor 812 is structured to be programmed with components to implement the functions described herein, such as those applying criteria to software version indicators.

The processor 812 of the illustrated example includes a local memory 813 (e.g., a cache). The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 816 may be implemented by flash memory and/or any other desired type of memory device. Access to the main memory 814, 816 is controlled by a memory controller.

The processor platform 800 of the illustrated example also includes an interface circuit 820. The interface circuit 820 may be implemented by any type of interface standard, such as those described hereinabove.

In the illustrated example, one or more input devices 822 are connected to the interface circuit 820. The input device(s) 822 permit(s) a user to enter data and commands into the processor 812. The input device(s) can be implemented by, for example, an audio sensor, a microphone, a camera (still or video), a keyboard, a button, a mouse, a touchscreen, a track-pad, a trackball and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

Coded instructions 832 representing the flow diagram of FIG. 9 or other steps described herein may be stored in the mass storage device 828, in the volatile memory 814, in the non-volatile memory 816, and/or on a removable tangible computer readable storage medium such as a CD or DVD.

Certain embodiments contemplate methods, systems and computer program products on any tangible machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system. Tangible computer readable media include a memory, DVD, CD, etc. storing the software and/or firmware, but do not include a propagating signal.

Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

Certain embodiments described herein can omit one or more of the method steps and/or perform the steps in a different order than the order listed. For example, some steps cannot be performed in certain embodiments. As a further example, certain steps can be performed in a different temporal order, including simultaneously, than listed above.

While the exemplary embodiments have been described with reference to an infusion pump, the teachings herein may be applied to other medical devices, such as apheresis devices (e.g., plasmapheresis, blood therapy, etc.) or other devices that are invasive or noninvasive, that interface with a human patient via a needle in the patient's skin, insulin pumps (e.g., internal or external to the body cavity), medical imaging devices (e.g., CT scanners, x-ray imagers, magnetic resonance imaging). The teachings may also be applied outside the medical field to any computing devices, such as mobile phones, tablet computers or other computers configured to be operated while held in a human hand, laptops, personal computers, and other networked computers.

Certain examples facilitate management of medical devices including blood collection or apheresis devices, infusion pumps, drug delivery pumps, and/or other medical devices. For example, an infusion pump infuses fluids, medication, or nutrients into a patient. An infusion pump can be used intravenously, subcutaneously, arterially, and/or epidurally, for example. For example, an infusion pump can administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) provides input to patient devices regarding type of infusion, mode, and/or other device parameter. For example, continuous infusion provides small pulses of infusion (e.g., between 500 nanoliters and 10 milliliters), with a pulse rate based on a programmed infusion speed. Intermittent infusion alternates between a high infusion rate and a low infusion rate with timing programmable to keep a cannula open, for example. Patient-controlled infusion provides on-demand infusion with a preprogrammed ceiling to avoid patient intoxication. The infusion rate is controlled by a pressure pad or button that can be activated by the patient, for example. Infusion pumps can include large volume pumps (e.g., for nutrient solution delivery to feed a patient), small-volume pumps (e.g., for medicine delivery), etc.

Certain examples determine and/or update a data set distribution policy associated with a medical device data management system (such as the Fenwal DXT™ data management system manufactured by Fenwal™, a Fresenius Kabi company). If a data set distribution policy has been created, then a new or updated data set (e.g., a new or updated drug library) can be distributed to one or more medical devices, even if one or more of the target medical devices are currently operating (e.g., pump(s) are currently infusing drug into a patient). Thus, data set distribution does not impact the pump's activity.

In certain examples, a data set defines a drug library and/or instruction set for a medical device such as a "smart" infusion pump, apheresis device, etc. For example, "smart" infusion pumps utilize a drug library or other close error reduction software to perform functions that assist healthcare providers with programming and calculating drug dose and delivery rates. The drug library is a database or data set that stores drug dosing information, including dosing limits, concentration, infusion parameters, and drug specific advisories, for example. Drug library instructions can help reduce or prevent medication errors and associated patient harm, for example.

Distribution of a data set to medical devices can occur directly at the device and/or remotely over a network (e.g., from a data management system to multiple medical devices, etc.).

In certain examples, a pharmacy controls the data set and distribution, and the end user (e.g., nurse, technician, etc.) is not given decision-making authority but must accept the data set to continue using the device. The device management system sends out a data set, and a receiving device is configured to activate the new data set on next reboot. The downloaded data set is held in a download buffer, for example, and, once the device is powered on, the device programs the data set into active memory. The user is then informed of the new data set and instructed to use the device or turn the device off but cannot revert to a prior version of the data set.

While the embodiments have been described with reference to certain details, it will be understood by those skilled in the art that various changes can be made and equivalents can be substituted without departing from the scope described herein. In addition, many modifications can be made to adapt a particular situation or material to the teachings without departing from its scope. Therefore, it is intended that the teachings herein not be limited to the particular embodiments disclosed, but rather include additional embodiments falling within the scope of the appended claims.

The invention claimed is:

1. A distribution server for downloading data sets to patient devices, comprising:
   a network interface circuit configured to communicate over a network with the patient devices;
   a memory coupled to the network interface circuit, the memory configured to receive over the network interface circuit a data set, the data set comprising parameters to be used by software on the patient devices to perform patient-related functions, the data set comprising a software version indicator for the data set, which software version indicator indicates compatibility between the data set and a plurality of software versions, the memory further configured to receive a current software version of a patient device; and a processing circuit configured to:

compare the software version indicator for the data set to the current software version of the patient device;

determine an inequality exists between the software version indicator for the data set and the current software version of the patient device; and distribute the data set to the patient device based on the determination of the inequality.

2. The distribution server of claim 1, wherein the patient devices are clinician-programmable infusion pumps, wherein the data set comprises hard and soft limits for parameters to be programmed by a clinician.

3. The distribution server of claim 1, wherein the processing circuit is configured to determine the inequality exists if the software version indicator for the data set is numerically less than or equal to the current software version of the patient device.

4. The distribution server of claim 1, wherein the software version indicator for the data set and current software version of the patient device each comprise a first software version code and a second software version code, wherein the data set is distributed to the patient device based on a determination that the first software version codes are equivalent and the second software version codes have the inequality.

5. The distribution server of claim 4, wherein the first software version code is a major software version code and the second software version code is a minor software version code.

6. The distribution server of claim 5, wherein the major software version code indicates an update in pump controls or pump mechanics, and wherein the minor software version code indicates an update in pump functionality not related to the data set.

7. The distribution server of claim 1, wherein the software version indicator for the data set and the current software version of the patient device each comprise a first function code associated with software operating a first set of functions on the patient device and second function code associated with software operating a second set of functions on the patient device.

8. The distribution server of claim 7, wherein the data set is distributed to the patient device based on a determination that the inequality exists for both the first function codes and the second function codes.

9. The distribution server of claim 1, wherein the software version indicator is associated with a plurality of software versions.

10. The distribution server of claim 9, wherein the software version indicator is associated with all software versions with which the data set is operable.

11. A distribution server for downloading data sets to patient devices, comprising:

a network interface circuit configured to communicate over a network with the patient devices;

a memory coupled to the network interface circuit, the memory configured to receive over the network interface circuit a data set, the data set comprising parameters to be used by software on the patient devices to perform patient-related functions, the data set comprising a software version indicator for the data set, the memory further configured to receive a current software version of a patient device; and a processing circuit configured to:

compare the software version indicator for the data set to the current software version of the patient device;

determine an inequality exists between the software version indicator for the data set and the current software version of the patient device;

distribute the data set to the patient device based on the determination of the inequality;

receive an indication that the patient device has an updated software version;

compare the updated software version to a plurality of data sets in the memory, each data set having a different software version indicator;

determine at least one data set having a software version indicator which is numerically less than or equal to the updated software version; and distribute the data set to the patient device based on the determination that the software version indicator is numerically less than or equal to the updated software version.

12. The distribution server of claim 11, wherein the processing circuit is configured to compare, determine and distribute as recited in claim 11 without requiring manual user input.

13. A distribution server for downloading data sets to patient devices, comprising:

a network interface circuit configured to communicate over a network with the patient devices;

a memory coupled to the network interface circuit, the memory configured to receive over the network interface circuit a data set, the data set comprising parameters to be used by software on the patient devices to perform patient-related functions, the data set comprising a software version indicator for the data set, which software version indicator indicates compatibility between the data set and a plurality of software versions, the memory further configured to receive a current software version of a patient device; and a processing circuit configured to:

compare the software version indicator for the data set to the current software version of the patient device;

determine the data set is not to be distributed to the patient device based on the comparison;

receive an indication that the patient device has an updated software version;

without receiving manual user input, automatically compare the software version indicator of the data set to the updated software version, determine the data set is to be distributed to the patient device based on the comparison to the updated software version, and distribute the data set to the patient device based on the determination that the data set is to be distributed to the patient device.

14. The distribution server of claim 13, wherein the patient devices are clinician-programmable infusion pumps, wherein the data set comprises hard and soft limits for parameters to be programmed by a clinician.

15. The distribution server of claim 13, wherein the processing circuit is configured to determine the data set is to be distributed to the patient device in the case where an inequality exists between the software version indicator for the data set and the updated software version.

16. The distribution server of claim 13, wherein the memory is configured to store a plurality of data sets, each having respective software version indicators, wherein the processing circuit is configured to identify at least two data sets compatible with the patient device, wherein the processing circuit is configured to distribute one of the two data sets having a greater software version indicator than the other of the two data sets.

17. The distribution server of claim 13, wherein the data set further comprises a device type indicating a type of patient device, wherein the software version indicator for the data set and updated software version of the patient device each comprise a first software version code and a second software version code, wherein the data set is distributed to the patient device based on a determination that the first software version codes are equivalent and the second software version codes have an inequality.

18. The distribution server of claim 13, wherein the software version indicator is associated with a plurality of software versions.

19. The distribution server of claim 18, wherein the software version indicator is associated with all software versions with which the data set is operable.

20. The distribution server of claim 13, wherein the processing circuit is configured to:
 compare the updated software version to a plurality of data sets in the memory, each data set having a different software version indicator and the plurality of data sets including the data set;
 determine at least one data set having a software version indicator which is numerically less than or equal to the updated software version; and
 distribute the data set to the patient device based on the determination that the software version indicator is numerically less than or equal to the updated software version.

* * * * *